United States Patent
Lee et al.

(10) Patent No.: US 12,429,408 B2
(45) Date of Patent: Sep. 30, 2025

(54) TESTING FIXTURE, SYSTEM, AND METHOD THEREOF

(71) Applicant: Coherex Medical, Inc., Salt Lake City, UT (US)

(72) Inventors: Sung K. Lee, Salt Lake City, UT (US); Tom Ditter, Mission Viejo, CA (US); Annabel Lee, Salt Lake City, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 241 days.

(21) Appl. No.: 18/079,861

(22) Filed: Dec. 12, 2022

(65) Prior Publication Data
US 2024/0192104 A1    Jun. 13, 2024

(51) Int. Cl.
*G01N 3/36* (2006.01)
*A61B 17/00* (2006.01)
*G01N 3/06* (2006.01)

(52) U.S. Cl.
CPC ............... *G01N 3/36* (2013.01); *G01N 3/066* (2013.01); *A61B 2017/00725* (2013.01); *G01N 2203/0005* (2013.01); *G01N 2203/0617* (2013.01)

(58) Field of Classification Search
CPC . G01N 3/36; G01N 3/066; A61B 2017/00725
See application file for complete search history.

(56) References Cited

U.S. PATENT DOCUMENTS

| | | | |
|---|---|---|---|
| 4,192,194 A | 3/1980 | Holt | |
| 7,254,988 B2 | 8/2007 | Keeble | |
| 7,621,192 B2 | 11/2009 | Conti et al. | |
| 9,237,935 B2 | 1/2016 | McCloskey et al. | |
| 10,627,315 B2 | 4/2020 | Conti et al. | |
| 2007/0068274 A1 | 3/2007 | Olson et al. | |
| 2020/0253735 A1* | 8/2020 | Lee | A61F 2/2472 |
| 2022/0236157 A1 | 7/2022 | Aravelli et al. | |

FOREIGN PATENT DOCUMENTS

| | | |
|---|---|---|
| DE | 19903476 | 8/2000 |
| WO | 2020236478 | 11/2020 |

OTHER PUBLICATIONS

Questmed Skills / Expertise, Dr. Christian Abicht, Questmed (Jun. 18, 2021).

(Continued)

*Primary Examiner* — Paul M. West
(74) *Attorney, Agent, or Firm* — David L. Stott (57) ABSTRACT

A durability testing fixture, system and method for testing a medical device. The testing fixture include a stabilizing member, an inflatable member and a pressure controller. The inflatable member is positioned adjacent the stabilizing member and defines a bore therein, the bore sized to hold the medical device. The inflatable member is configured to receive and release a fluid so that the inflatable member is respectively inflatable and deflatable to radially displace an inner surface of the bore. The pressure controller is coupled to the inflatable member and is configured to control inflation and deflation of the inflatable member to radially displace the inner surface of the bore and to apply a force directly along an outer radially extending surface of the medical device.

17 Claims, 7 Drawing Sheets

(56) References Cited

OTHER PUBLICATIONS

International Search Report dated Mar. 12, 2024 for International Application No. PCT/IB2023/062381 (16 pages).
Laasch Hans-Ulrich et al., "'Radial force' of colonic stents: A parameter without consistency, definition or standard," International Journal of Gastrointestinal Intervention, vol. 9, No. 3 (Jul. 31, 2020).

* cited by examiner

TESTING FIXTURE, SYSTEM, AND METHOD THEREOF

TECHNICAL FIELD

The present invention relates generally to testing fixtures and, more specifically, to durability and fatigue life testing fixtures for medical devices.

BACKGROUND

The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages don't appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

One current challenge found in the development of medical device implants involves testing the durability of such medical device implants. One reason this is challenging and complex is because it is difficult to mimic the anatomical motion found, for example, in the ostium of the left atrial appendage of the heart. The current testing fixtures for testing durability use uniaxial motion, applying displacement onto the implant uniaxially at an axis or sequence of uniaxial motions. As such, the uniaxial motion employed by current available testing fixtures does not simulate motion applied and produced by, for example, the human heart. Therefore, the current testing fixtures do not simulate realistic anatomical motion to test the durability of a given medical device implant.

BRIEF SUMMARY OF THE INVENTION

The present invention is directed to a durability testing fixture configured to test a medical device, the medical device having a hub and a framework such that the framework extends radially from the hub. The testing fixture includes a stabilizing member, an inflatable member and a pressure controller. The inflatable member is positioned adjacent the stabilizing member, the inflatable member extending to define a bore therein such that the bore is sized and configured to position the medical device within the bore so that an inner surface of the inflatable member that defines the bore engages an outer radially extending surface of the medical device. The inflatable member is configured to receive and release a fluid so that the inflatable member is respectively inflatable and deflatable to radially displace the inner surface of the bore. The pressure controller is coupled to the inflatable member, the pressure controller configured to control inflation and deflation of the inflatable member to radially displace the inner surface of the bore and to apply a force directly along the outer radially extending surface of the medical device.

In another embodiment, the bore is sized and configured to surround the outer radially extending surface of the medical device such that the inner surface radially engages the medical device. In another embodiment, the inflatable member extends with multiple chambers defined therein. In still another embodiment, the inflatable member includes one or more sensors associated therewith.

In another embodiment, the inflatable member extends with a wall, the wall extending with a first thickness and a second thickness, the second thickness being smaller than the first thickness. In a further embodiment, upon the inflatable member being inflated, the inflatable member exhibits a convex structure along the second thickness of the wall of the inflatable member. In still another embodiment, upon the inflatable member being inflated, the inflatable member exhibits a convex structure along the inner surface of the inflatable member. In yet another embodiment, upon the inflatable member being inflated and deflated by the pressure controller, the bore of the inflatable member is moved between a first diameter and a second diameter.

In accordance with another embodiment of the present invention, a testing system for testing a medical device, the medical device having a hub and a framework such that the framework extends radially from the hub, is provided. The testing system includes a computing device, a pressure controller, a stabilizing member, and an inflatable member. The computing device includes one or more processors. The pressure controller is coupled to the computing device, the pressure controller including a fluid line associated therewith. The inflatable member is positioned adjacent the stabilizing member, the inflatable member extending to define a bore therein such that the bore is sized and configured to position the medical device within the bore so that an inner surface of the inflatable member that defines the bore engages an outer radially extending surface of the medical device. The inflatable member is configured to receive and release a fluid so that the inflatable member is respectively inflatable and deflatable to radially displace the inner surface of the bore. With this arrangement, the pressure controller is coupled to the inflatable member with the fluid line, the pressure controller configured to control inflation and deflation of the inflatable member to radially displace the inner surface of the bore and to apply a force directly along the outer radially extending surface of the medical device.

In another embodiment, the bore is sized and configured to surround the outer radially extending surface of the medical device such that the inner surface radially engages the medical device. In another embodiment, the inflatable member extends with multiple chambers defined therein. In still another embodiment, the inflatable member includes one or more sensors associated therewith.

In another embodiment, the inflatable member extends with a wall, the wall extending with a first thickness and a second thickness, the second thickness being smaller than the first thickness; and wherein, upon the inflatable member being inflated, the inflatable member exhibits a convex structure along the second thickness of the wall of the inflatable member. In yet another embodiment, upon the inflatable member being inflated, the inflatable member exhibits a convex structure along the inner surface of the inflatable member. In another embodiment, upon the inflatable member being inflated and deflated by the pressure controller, the bore of the inflatable member is moved between a first diameter and a second diameter.

In accordance with another embodiment of the present invention, a method for testing the durability of a medical device is provided. The method steps includes: providing a fixture including a stabilizing member and an inflatable member, the inflatable member positioned adjacent the stabilizing member, the inflatable member extending to define a bore therein; positioning the medical device within the bore of the inflatable member so that an inner surface of the inflatable member that defines the bore engages an outer radially extending surface of the medical device; and radially displacing the inner surface of the bore with a pressure controller coupled to the inflatable member such that fluid inflates and deflates the inflatable member to apply a radial force directly along the outer radially extending surface of the medical device.

In another embodiment, the method further includes sequentially inflating and deflating the inflatable member with multiple chambers defined in the inflatable member. In still another embodiment, the radially displacing step includes repeatedly radially displacing the inner surface of the inflatable member to repeatedly radially displace portions of the medical device. In another embodiment, the method further includes sensing a radial force placed upon the medical device with one or more sensors associated with the inflatable member. In another embodiment, the method further includes controlling a cycle rate by which the inflatable member is inflated and deflated and tracking the number of cycles with a computing device.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
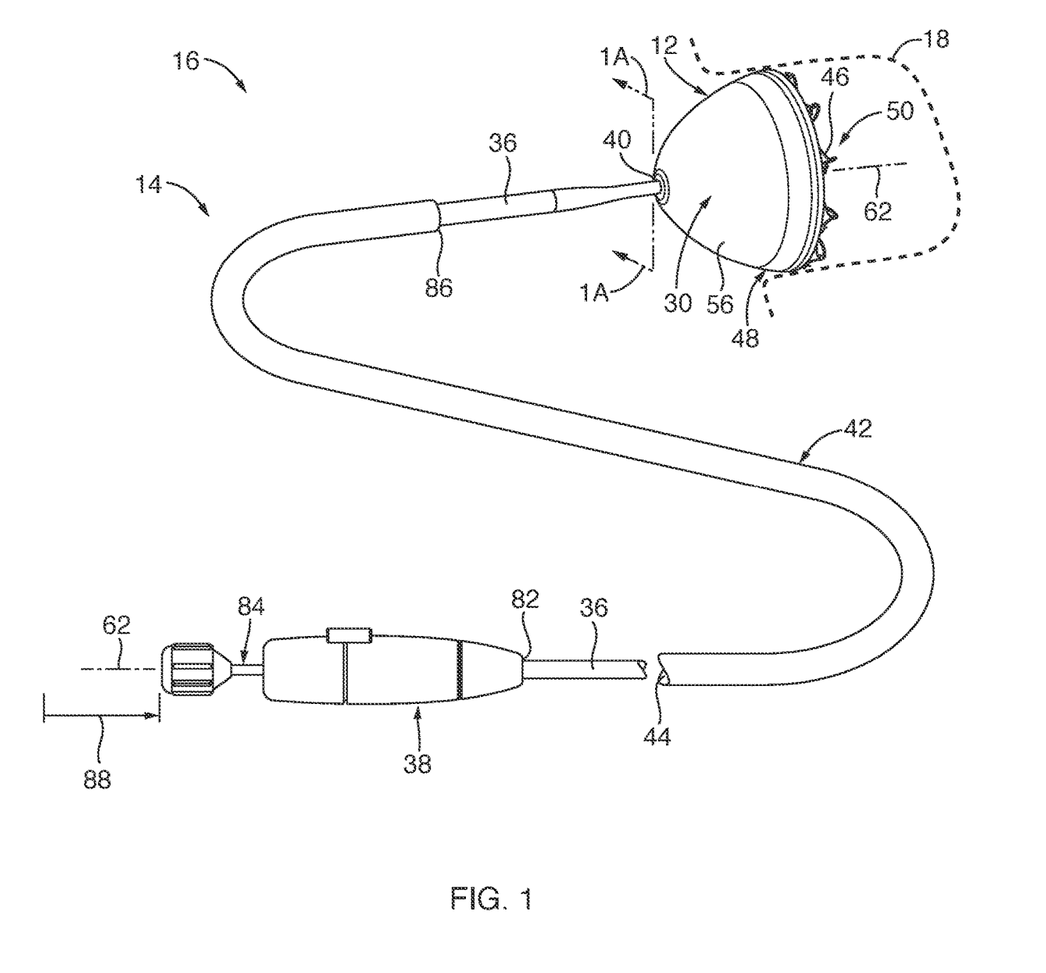
FIG. 1 is a perspective view of a medical device system, depicting an implant coupled to a delivery system, according to one embodiment of the present invention.
Figure 5:
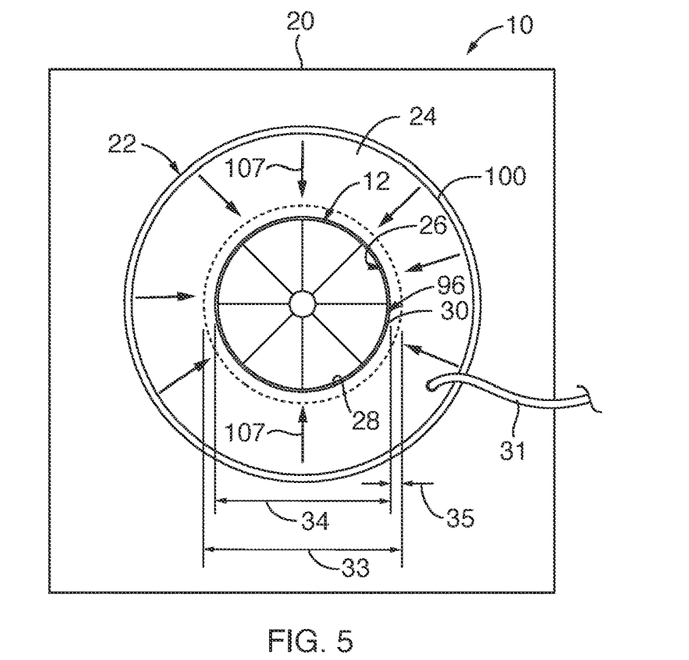
FIG. 5 is a top view of the testing fixture, depicting the implant positioned within the bore so that the inflatable member radially surrounds the implant, according to another embodiment of the present invention.

Referring to FIGS. 1 and 5, a testing fixture 10 may be sized and configured to test the durability and fatigue life of, for example, a medical device. Further, such testing fixture 10 may also be employed with any other suitably sized device needing to be tested to understand its fatigue life or better understand its mechanical characteristics and how to improve the structural characteristics of a given medical device. For example, one medical device that may be employed with the testing fixture 10 is an implant 12. Such an implant 12 may be the type that is employed in interventional procedures for percutaneously closing and modifying an opening such as, for example, a left atrial appendage 18 within a heart (not shown). Further, the implant 12 may be the type that is permanently implanted into the human anatomy and, therefore, the implant may be removably coupled to a delivery system 14 such that the delivery system 14 and implant 12 together may define a medical device system 16. The fixture 10 may include a stabilizing member 20 and an inflatable member. The stabilizing member may be sized and configured to maintain a fixed position. The inflatable member may be positioned adjacent the stabilizing member. In one embodiment, the stabilizing member may extend to define a cavity 22 therein such that the inflatable member 24 may be positioned within the cavity 22. The inflatable member 24 may extend to define a bore 26 therein. Such bore 26 may be sized and configured to position the implant 12 within the bore 26 so that an inner surface 28 of the inflatable member 24 may engage with an outer surface 30 of the implant 12. Further, the inflatable member 24 may be configured to inflate with the introduction of a fluid, such as air or liquid, and deflate with the release of the fluid. The fixture may also include a pressure controller 32 that may be operatively coupled to the inflatable member 24. The pressure controller 32 may be configured to control the fluid introduced and released relative to the inflatable member 24 such that the inner surface of the inflatable member may be radially displaced to bias against the outer surface, such as a circumference or radially extending periphery, of the implant 12.

Figure 1A:
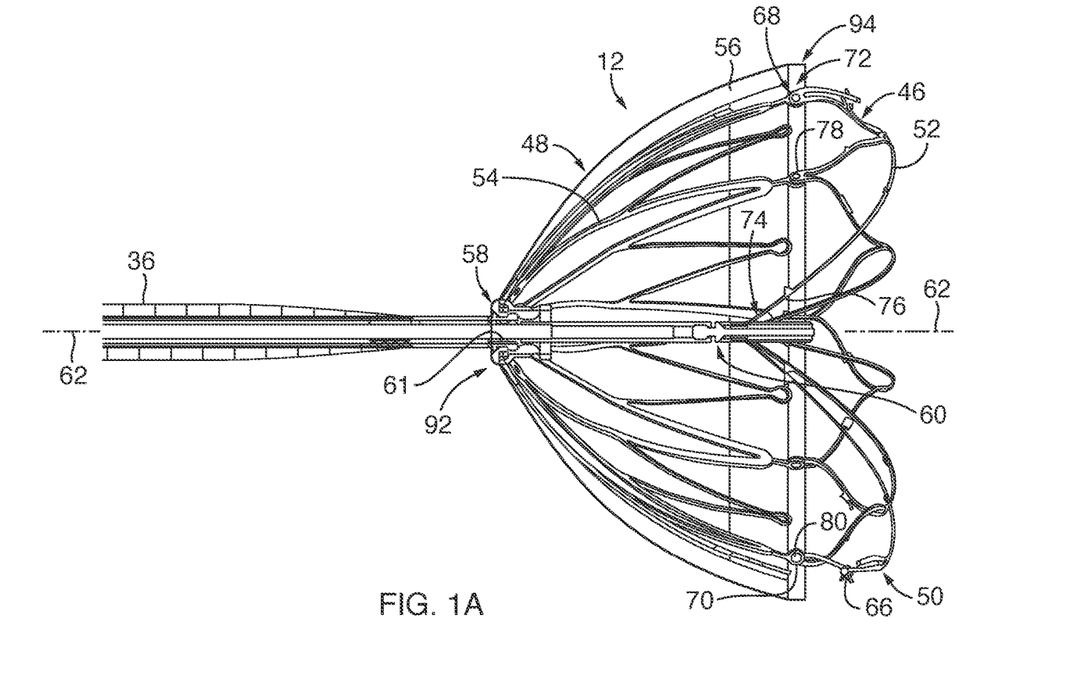
FIG. 1A is a partial cross-sectional view of the medical device system taken along section line 1A-1A of FIG. 1, depicting the implant in a deployed position, according to another embodiment of the present invention.

Now with reference to FIGS. 1, 1A, 2, and 2A, as previously set forth, the medical device system 16 includes the delivery system 14 and the implant 12 such that the implant 12 may be removably coupled to the delivery system 14. Further, the medical device system 16 may be employed in interventional procedures for percutaneously closing and modifying an opening such as, for example, a left atrial appendage 18 within a heart (not shown). The delivery system 14 may include a pusher catheter 36 and a handle 38, the pusher catheter 36 being coupled to the implant 12 adjacent a distal end 40 of the pusher catheter 36. Also, the delivery system 14 may include a sheath 42 sized and configured to facilitate advancing the implant 12 through a lumen 44 of the sheath 42 with the pusher catheter 36 (see also FIG. 3). In addition, the implant 12 may extend to define a framework 46 extending along an occluder portion 48 and an anchor portion 50. The anchor portion 50 may extend with an anchor frame 52 and the occluder portion 48 may include an occluder frame 54 with a tissue growth member 56 attached to the occluder frame 54. The implant 12 may include a primary hub 58 and a secondary hub 60 such that the framework 46 may extend between the primary hub 58 and the secondary hub 60. The primary hub 58 may define a bore hub 61 and an axis 62 that each may extend through the primary hub 58 such that the axis 62 may extend axially relative to the bore hub 61 and structure of the primary hub 58. Such axis 62 may also extend axially along a length of the delivery system 14 and the components thereof. Further, the secondary hub 60 may be moveable along the axis 62 through the primary hub 58 so as to move the framework 46 between a constricted position (FIG. 2A) and a deployed position (FIG. 1A). With this arrangement, as the secondary hub 60 moves along the axis 62 and through the bore hub 61 of the primary hub 58, the framework 46 may be minimized radially as the framework 46 moves between the constricted and deployed positions. Furthermore, upon the framework 46 at least partially being constricted within the sheath 42, the framework 46 may extend with structure that may minimize resistance with an internal surface of the sheath 42.

As previously set forth, the framework 46 may extend with the occluder portion 48 to define the occluder frame 54 and the framework 46 may extend with the anchor portion 50 to define the anchor frame 52. The anchor frame 52 may extend with the anchor portion 50 and define anchor tines 66 extending therefrom. The occluder frame 54 may extend with the occluder portion 48 with the tissue growth member 56 attached to the occluder frame 54. The tissue growth member 56 may be in the form of an occlusive member, but may also be in the form of a filter member, a mesh member, a membrane or any other structure, or combinations thereof, sized and configured to promote tissue in-growth. Further, the tissue growth member 56 may be formed from one or more polymeric materials, such as ePTFE and/or a polyurethane foam, or any other suitable polymeric material. Even further, the tissue growth member 56 may extend with multiple layers with varying thicknesses and sizes.

Further, the occluder frame 54 may be coupled to the primary hub 58 such that the occluder frame 54 may extend radially outward from the primary hub 58 and may extend distally to an occluder frame distal end 68. Adjacent to the occluder frame distal end 68, the occluder frame 54 may include multiple occluder frame eyelets 70 defined in the occluder frame 54. The anchor frame 52 may extend between a first anchor frame end 72 and a second anchor frame end 74, the first anchor frame end 72 coupled to the occluder frame 54 and the second anchor frame end 74 coupled to the secondary hub 60. The anchor frame 52 may extend with multiple anchor frame segments 76, interconnected to each other, extending between the first and second anchor frame ends 72, 74 of the anchor frame 52. Adjacent to the first anchor frame end 72 of the anchor frame 52, the anchor frame 52 may include multiple anchor frame eyelets 78 along multiple ones of the anchor frame segments 76 of the anchor frame 52. At the secondary hub 60, multiple ones of the anchor frame segments 76 or anchor frame extensions may be coupled to the secondary hub 60. Each of the occluder frame eyelets 70 may be coupled to a corresponding one of the anchor frame eyelets 78 with a hinge component 80. The hinge component 80 may extend through the occluder frame eyelet 70 and the anchor frame eyelet 78 so as to facilitate the anchor frame 52 to pivot about the hinge component 80 so as to pivot or rotate relative to the occluder frame 54. With this arrangement, the anchor frame 52 may be pivotably coupled (or hingeably coupled) to the occluder frame 54 so that the anchor frame 52 may move between a retracted position (FIG. 2A) and a deployed position (FIG. 1A). The retracted position of the anchor frame 52 may also be an anchor constrained position or pivoted position. As such, the pivoting between the retracted and deployed positions of the anchor frame 52 may assist a physician in adjusting the position of the implant 12 subsequent to the anchor portion 50 being secured to tissue in, for example, the left atrial appendage 18.

Figure 2:
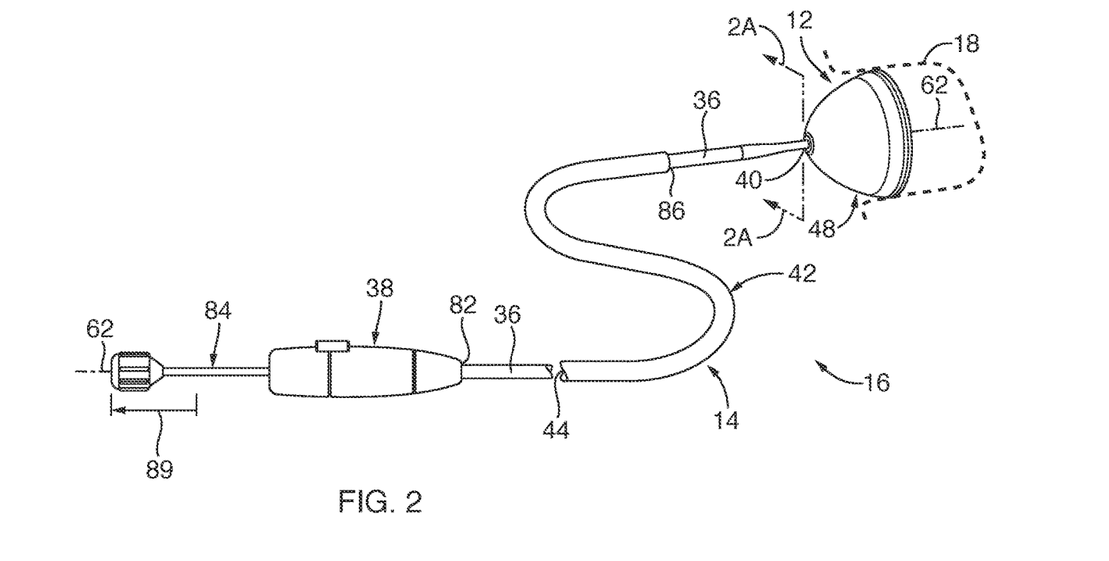
FIG. 2 is a perspective view of the medical device system, depicting the implant in a partially deployed position, according to another embodiment of the present invention.
Figure 2A:
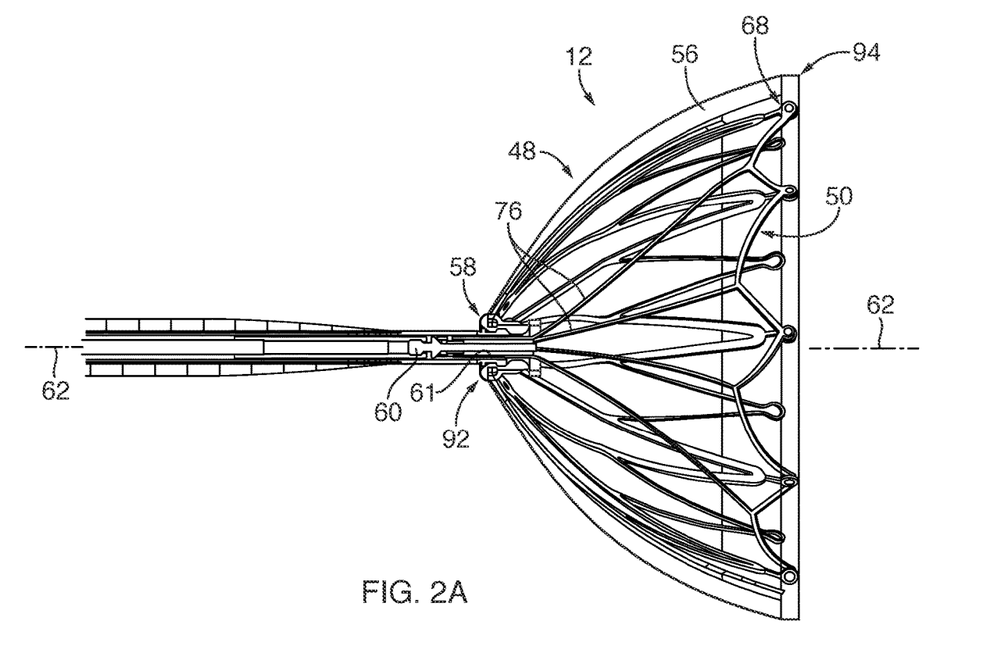
FIG. 2A is a partial cross-sectional view of the medical device system taken along section line 2A-2A of FIG. 2, depicting anchors of the implant in a retracted position, according to another embodiment of the invention.
Figure 3:
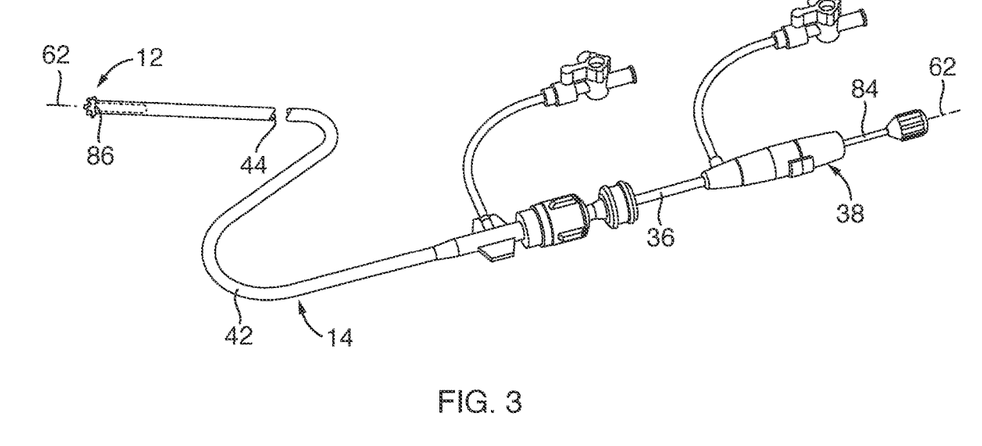
FIG. 3 is a perspective view of the medical device system, depicting the implant being at least partially constricted within a sheath of the medical device system, according to another embodiment of the present invention.

With reference to FIGS. 1-3, as previously set forth, the implant 12 may be delivered through the vasculature with the delivery system 14. The delivery system 14 may include the pusher catheter 36 and the handle 38, the handle 38 integrated with a proximal portion 82 of the pusher catheter 36. The handle 38 may include various functional components, such as an anchor actuator 84, to manipulate the anchor frame 52 between the deployed position (FIG. 1A) and the retracted position (FIG. 2A). The delivery system 14 may include and be employed with the sheath 42 for delivering the implant 12 through the vasculature and to the left atrial appendage 18 in the heart. The sheath 42 may be positioned within the vasculature using known interventional techniques with a sheath distal end 86 to be positioned adjacent the left atrial appendage 18 of the heart. Upon the implant 12 being advanced through the lumen 44 of the sheath 42 to the sheath distal end 86 (the implant 12 being in the constricted position partially shown in dashed lines adjacent the sheath distal end 86 (see FIG. 3)), the implant 12 may at least partially be deployed from the sheath 42. That is, the sheath 42 may then be manually moved proximally (and/or the pusher catheter 36 advanced distally) so that the occluder portion 48 of the implant 12 may be deployed from the sheath distal end 86. Such occluder portion 48 may immediately self-expand as the occluder portion 48 is exposed from the sheath distal end 86. At this stage, the implant 12 may be in a partially deployed state, after which, the implant 12 may be moved to a fully deployed state by deploying the anchor portion 50, as depicted in FIG. 1. For example, upon the occluder portion 48 initially being deployed, the anchor portion 50 may be in the retracted position with the anchor actuator 84 of the handle 38 in the proximal position, as depicted in FIG. 2. Once a physician determines that the occluder portion 48 is in an appropriate and desired position adjacent the left atrial appendage 18, the anchor portion 50 may be pivoted from the retracted position to the deployed position by moving the anchor actuator 84 to the distal position, as shown by arrow 88 (see FIG. 1). Once the anchor portion 50 is moved to the deployed position, the anchor tines 66 (FIG. 1A) of the anchor portion 50 may engage tissue to secure the implant 12 in the left atrial appendage 18. If the physician determines that the implant 12 is not in an optimal secured position in the left atrial appendage 18, the anchor portion 50 may be pivoted back to the retracted position by moving the anchor actuator 84 from the distal position, to the proximal position, as shown by arrow 89 in FIG. 2. As such, the anchor actuator 84 may be manually moved proximally and distally to move the anchor portion 50 between the retracted and deployed positions such that the anchor portion 50 pivots between the deployed and retracted positions. In this manner, the anchor portion 50 of the implant 12 may be secured and disengaged from tissue in the left atrial appendage 18 as needed by the physician until the physician obtains an optimal position or is satisfied with its position prior to releasing the delivery system 14 from the implant 12. Additional disclosure of a similar medical device delivery system is disclosed in commonly assigned U.S. patent application Ser. No. 15/438,650, filed on Feb. 21, 2017, now issued as U.S. Pat. No. 10,631,969, entitled MEDICAL DEVICE FOR MODIFICATION OF LEFT ATRIAL APPENDAGE AND RELATED SYSTEMS AND METHODS, the disclosure of which is incorporated by reference herein in its entirety.

Figure 4:
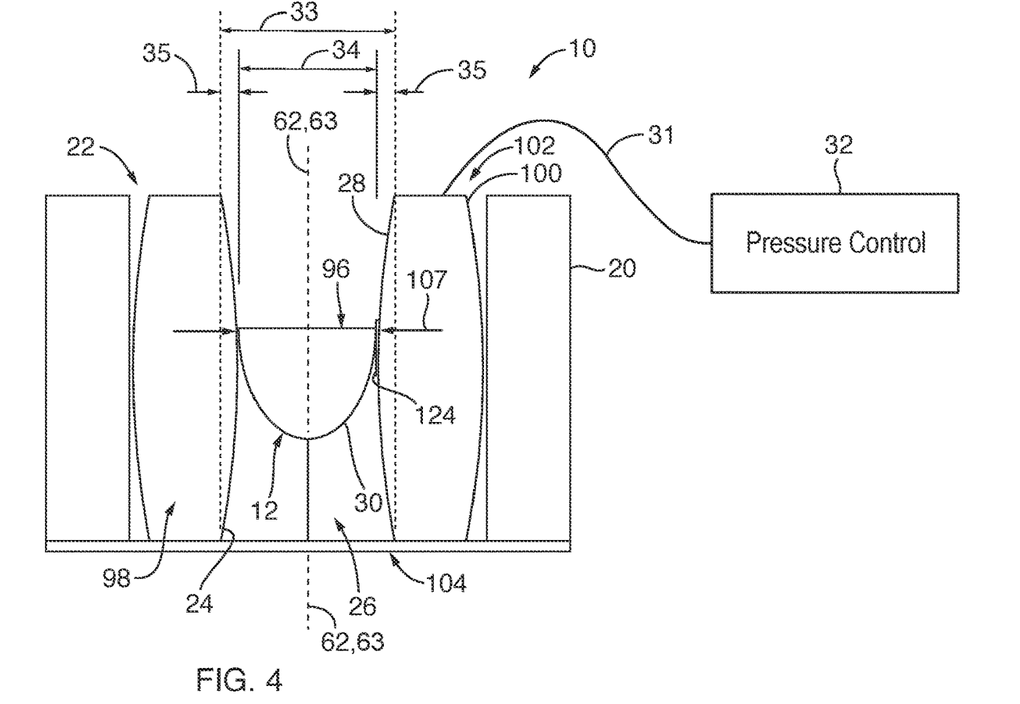
FIG. 4 is a simplistic side view of a testing fixture, depicting the implant positioned within a bore of an inflatable member of the testing fixture, according to another embodiment of the present invention.

Now with reference to FIGS. 4 and 5, as previously set forth, the fixture 10 may include a stabilizing member 20. The stabilizing member 20 may be in a fixed or secured position. The stabilizing member 20 may extend to define a circular or square outer profile or any other outer profile. In one embodiment, the stabilizing member 20 may extend to define the cavity 22 therein. The cavity 22 of the stabilizing member 20 may be sized and configured to hold and position the inflatable member 24 within the cavity 22. Further, the stabilizing member 20 may be referenced as a casing that may surround the inflatable member 24. The inflatable member may be secured to the stabilizing member such that the inflatable member 24 may be maintained adjacent to the stabilizing member. The inflatable member 24 may be sized and configured to extend adjacently along the stabilizing member 20 so that the inflatable member defines the bore 26 therein. The bore 26 may extend to define a first diameter 33 or first position. The first diameter 33 of the bore 26 may be sized and configured for the implant 12 to be positioned therein such that the inner surface 28 of the inflatable member 24 (or the surface that defines the bore 26) may surround an outer surface 30 or a circumference 96 (or radially extending periphery) of the implant 12. Further, the inner surface 28 of the inflatable member 24 may engage and hold the position of the implant 12 within the bore 26 in a similar manner as if the implant 12 was positioned within an opening in the anatomy, such as the ostium of the left atrial appendage 18 (FIG. 1) of the heart.

The inflatable member 24 may include an interior 98, the interior 98 being configured to receive a fluid therein via a fluid line 31 coupled to a pressure controller 32. The pressure controller 32 may be designed to control and move fluid through the fluid line 31 into and out of the inflatable member 24. Such movement of fluid into the inflatable member 24 may inflate the inflatable member 24 to a second position or second diameter 34, the second diameter 34 being smaller than the first diameter 33. Further, movement between the first and second positions or first and second diameters 33, 34 may be defined as radial displacement 35 of the inflatable member 24. As such, upon the implant 12 being positioned within the bore 26 of the inflatable member 24 and upon the inflatable member 24 being inflated to the second diameter 34, the inflatable member may apply a pressure and force radially around the outer surface 30 or circumference 96 of the implant 12. In this manner, the implant 12 may be positioned within the bore 26 of the inflatable member 24 in a fully expanded and deployed position, similar to the implant 12 position shown in FIGS. 1 and 1A, so that the implant 12 may be placed under radial pressure and radially displace portions of the implant 12 due to the radial displacement 35 of the inflatable member 24.

In one embodiment, the first position of the inflatable member 24 may be a relaxed position or a position filled with fluid to the extent to be sized to correspond with the position for which the implant 12 may be positioned within the bore 26 of the inflatable member 24. As such, the first position of the inflatable member 24 may exhibit the inflatable member being partially inflated or a relaxed, non-inflated position of the inflatable member. Further, the first position of the inflatable member may be a position where a radial pressure may not have been applied to the outer surface 30 of the implant 12.

The second position that corresponds with the second diameter 34 may be the position for which the inflatable member 24 has been inflated to radially displace the implant 12 positioned within the bore 26. In the second position, the fluid being injected into the interior 98 of the inflatable member 24, may displace the diameter 34 of the bore 26 such that the inner surface 28 and the diameter 34 of the bore 26 may move radially inward towards a fixture axis 63. Upon positioning the implant 12 within the bore 26 of the inflatable member, the fixture axis 63 may correspond with the axis 62 of the implant 12. Further, upon the inflatable member 24 being inflated, the inner surface 28 may extend with a curvature between a first end 102 and a second end 104 such that an outer side 100 and/or inner surface 28 of the inflatable member 24 may exhibit a convex curvature. In this manner, upon the implant 12 being positioned within the bore 26 of the inflatable member 24, the pressure controller 32 may repeatedly inflate and deflate the inflatable member 24 to move the inflatable member 24 between first and second positions or first and second diameters 33, 34 to repeatedly apply a radial force, as shown by arrows 107, upon the outer surface 30 or outer portions of the implant 12 to, thereby, simulate the radial forces of a beating heart.

The pressure controller 32 may control the pressure applied to the inflatable member 24 and further, to one or more chambers of the inflatable member 24, discussed further herein. In one embodiment, the pressure applied with the fluid may be introduced into the inflatable member 24 in a generally consistent or constant manner. In another embodiment, the pressure applied with the fluid may be introduced to the inflatable member 24 in a variable manner such that varying pressures may interact against the implant 12 as the inflatable member 24 inflates and deflates. Further, the diameter of the bore 26 may change or may vary along its length or along the depth of the bore 26 such that the diameter changes or the inflatable member 24 undergoes radial displacement to interact with the implant 12 positioned in the bore 26 of the inflatable member 24. Furthermore, the pressure controller 32 may be configured to control a rate for which the fluid is introduced and released into the inflatable member 24, for example, the pressure controller 32 may inject and extract the fluid in rapid succession or sequence such that the fixture 10 may test the fatigue and durability of the implant 12. For example, in the case of the implant being a medical device being permanently released in the heart, the step of inflating and deflating the inflatable member may define a single cycle, which may simulate or correspond to a single heart beat. The pressure control 32 may implement very rapid cycles of inflating and deflating the inflatable member 24 for long periods of time until a failure in the implant 12 is detected or sensed by one or more sensors 124. In this manner, upon detection of the implant 12 failing, the number of cycles will be known, which can then correlate to a general life of the implant within the human heart.

Figure 6:
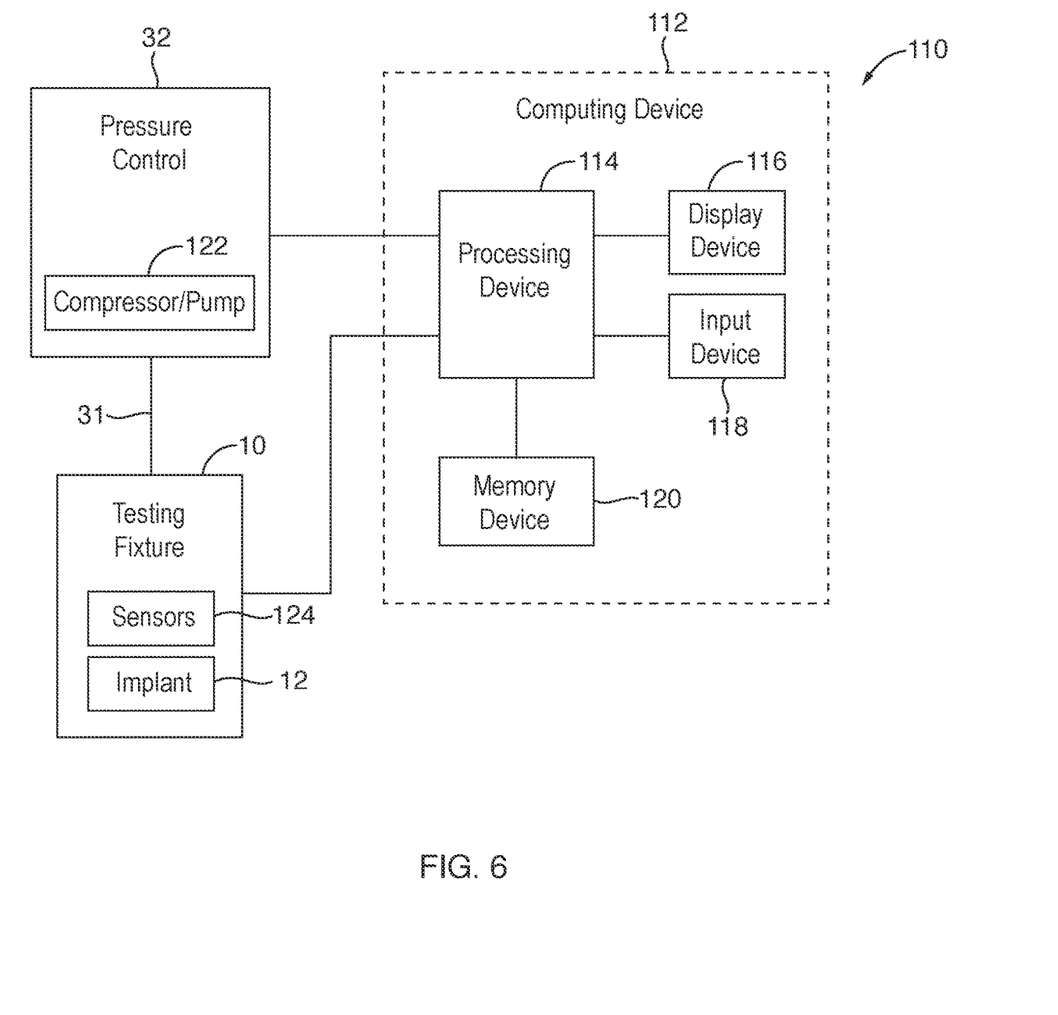
FIG. 6 is a block diagram of a testing fixture system, depicting the testing fixture coupled to a pressure control and a computing device, according to another invention of the present invention.

With reference to FIG. 6, in another embodiment, a testing fixture system 110 including the testing fixture 10, the pressure controller 32 and a computing device 112 is provided. The pressure controller 32 may be coupled to the computing device 112 and the testing fixture 10. The computing device 112 may include a processing device 114 or one or more processors. The computing device 112 may be a typical computer or the like, such as a desk-top computer, lap-top computer, or tablet. The processing device 114 may be coupled to a display device 116, an input device 118, and memory 120. The display device 116 may be a typical display associated with the computing device 112, such as a touch screen display, or any other type of display that allows a user to view detail or data, as known to one of ordinary skill in the art. The input device 118 may be a key board, a mouse controller, and/or a touch sensitive screen of the display device 116, for example. The memory 120 may include any suitable volatile and/or non-volatile memory, such as random accesses memory or a hard disk drive or the like. The pressure controller 32 may include a compressor 122 (or a similar device for moving and controlling fluid, such as a pump) such that the compressor 122 may be sized and configured to advance or withdraw fluid from the inflatable member 24 (FIG. 4) of the testing fixture 10 with the fluid line 31 (FIG. 4). The testing fixture 10 may also include one or more sensors 124 associated therewith that may be sized and configured to provide data about the inflatable member 24 and the implant 12 while the implant 12 is being tested in the fixture 10. For example, the inflatable member 24 may include the one or more sensors 124 thereon, as shown in FIG. 4. Further, such one or more sensors 124 may be pressure sensors. The pressure sensors may detect a pressure or radial force of the inflatable member employing a strip and measuring resistive voltage in the strip positioned on the inflatable member 24 (see FIG. 4), for example, as known to one of ordinary skill in the art. With this arrangement, the one or more sensors 124 may be coupled to the inflatable member 24 and associated with the implant 12 so as to be designed and configured to provide data to the computing device 112 so that, upon failure occurring to the implant 12, data may be transferred to the computing device so that detail regarding such failure to the implant 12, such as the total number of cycles at the time of the failure, may be better understood.

In another embodiment, the one or more sensors 124 associated with the inflatable member 24 may include a temperature sensor. Further, the fluid employed with the pressure control 32 for inflation and deflation of the inflatable member 24 may be heated to be consistent, for example, with the temperature of the human anatomy to better mimic the environment of an implant being positioned in the left atrial appendage of the heart, for example. As such, the temperature of the fluid may be controlled with a heater. Upon the temperature sensor detecting a lower temperature than that desired, the temperature sensor may send a signal to the computing device 112. The computing device 112 can then activate heaters for heating the fluid at the pressure control 32 so that the fluid temperature in the inflatable member 24 may increase to the desired temperature.

Figure 7:
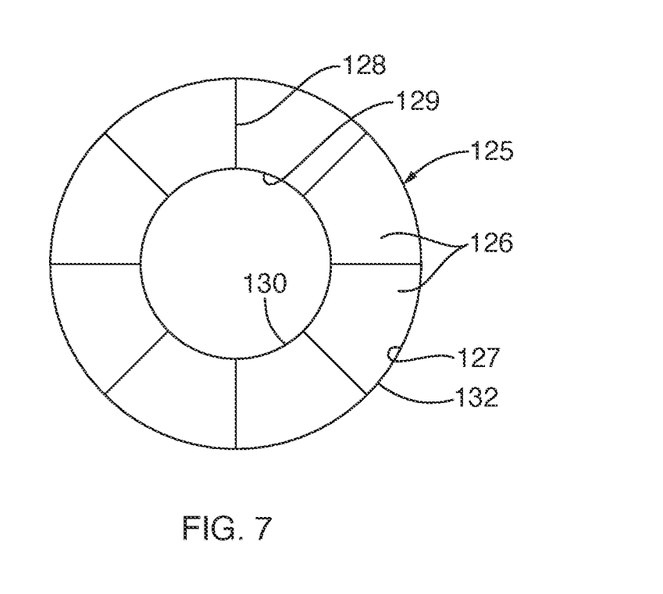
FIG. 7 is a simplistic top view of another embodiment of an inflatable member, depicting the inflatable member being separated into multiple chambers, according to another embodiment of the present invention.

Now with reference to FIG. 7, another embodiment of an inflatable member 125 with a bore 129 defined therein is provided. The inflatable member 125 may define multiple chambers 126 therein. The inflatable member 125 may extend with an interior 127 and side walls 128, the side walls 128 extending within the interior 127 to define the multiple chambers 126 within the interior of the inflatable member 24. The side walls 128 may extend between an inner surface 130 and outer surface of the inflatable member 125 such that the side walls 128 may extend radially from the inner surface 130 of the inflatable member 125. In a further embodiment, each of the multiple chambers 126 may be independently inflatable and deflatable such that each one of the chambers 126 may include its own fluid line 31 (FIG. 4). The multiple chambers 126 may be separated by the side walls 128 such that adjacent ones of the chambers 126 may include a common side wall 128. As such, adjacent ones of the multiple chambers 126 may be positioned laterally adjacent to each other. In another embodiment, some of the chambers 126 may be independently inflatable and deflatable and some of chambers 126 may be interconnected. In still another embodiment, each of chambers 126 may be interconnected. For example, in the embodiment where the multiple chambers 126 are interconnected, the multiple chambers 126 may be inflated and deflated in a sequential manner. In another embodiment, the multiple chambers 126 may be inflated and deflated in a variable manner. The multiple chambers 126 defined in the inflatable member 125 may generate various force profiles along the inner surface 130. Furthermore, the multiple chambers 126 may vary in size and/or some chambers may vary in pressure applied thereto so that radial forces applied to the implant 12 (see FIG. 5) may be different along different portions that contact the implant 12.

Figure 8:
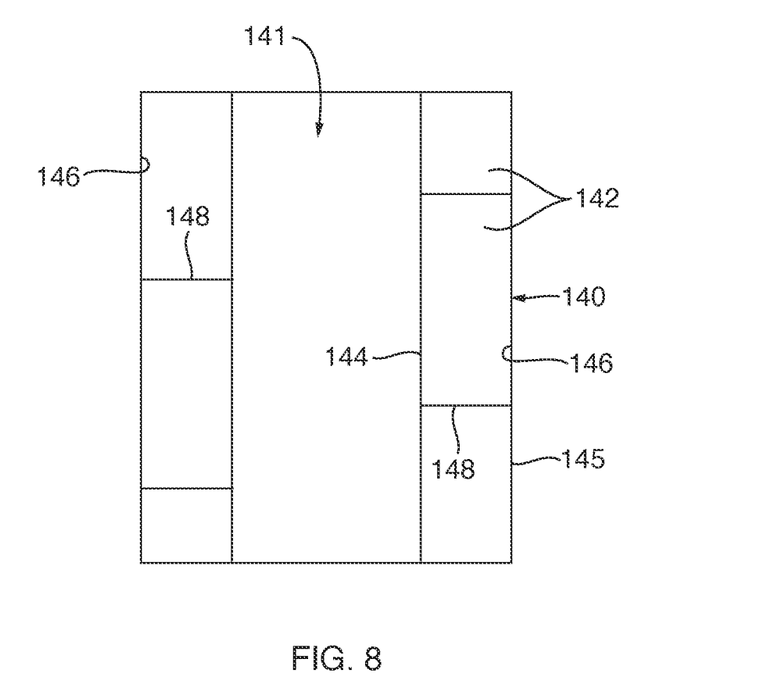
FIG. 8 is a simplistic side view of another embodiment of an inflatable member, depicting the inflatable member separated into multiple chambers, according to another embodiment of the present invention.

With reference to FIG. 8, another embodiment of an inflatable member 140 with a bore 141 defined therein is provided. In this embodiment, the inflatable member 140 includes multiple chambers 142 defined therein. The inflatable member 140 may include an inner surface 144 and an outer surface 145 defining an interior 146 therebetween. Further, the multiple chambers 142 may be separated with side walls 148, similar to the previous embodiment. In this embodiment, the side walls 148 may be oriented different from the previous embodiment such that the side walls 148 may extend between the inner surface 144 and the outer surface 145 to separate upper and lower chambers of the multiple chambers 142. Similar to the previous embodiment, each of the multiple chambers 142 may be independently inflatable and deflatable such that each one of the chambers 142 may include its own fluid line 31 (FIG. 4). In another embodiment, some of the chambers 142 may be independently inflatable and deflatable and some of chambers 142 may be interconnected. In still another embodiment, each of chambers 142 may be interconnected. For example, in the embodiment where the multiple chambers 142 are interconnected, the multiple chambers 142 may be inflated and deflated in a sequential manner. In another embodiment, the multiple chambers 142 may be inflated and deflated in a variable manner, as set forth in the previous embodiment. Further, in another embodiment, the multiple chambers 142 may be inflated and deflated in a generally consistent manner and with a consistent rate of cycles per minute, for example.

Figure 9:
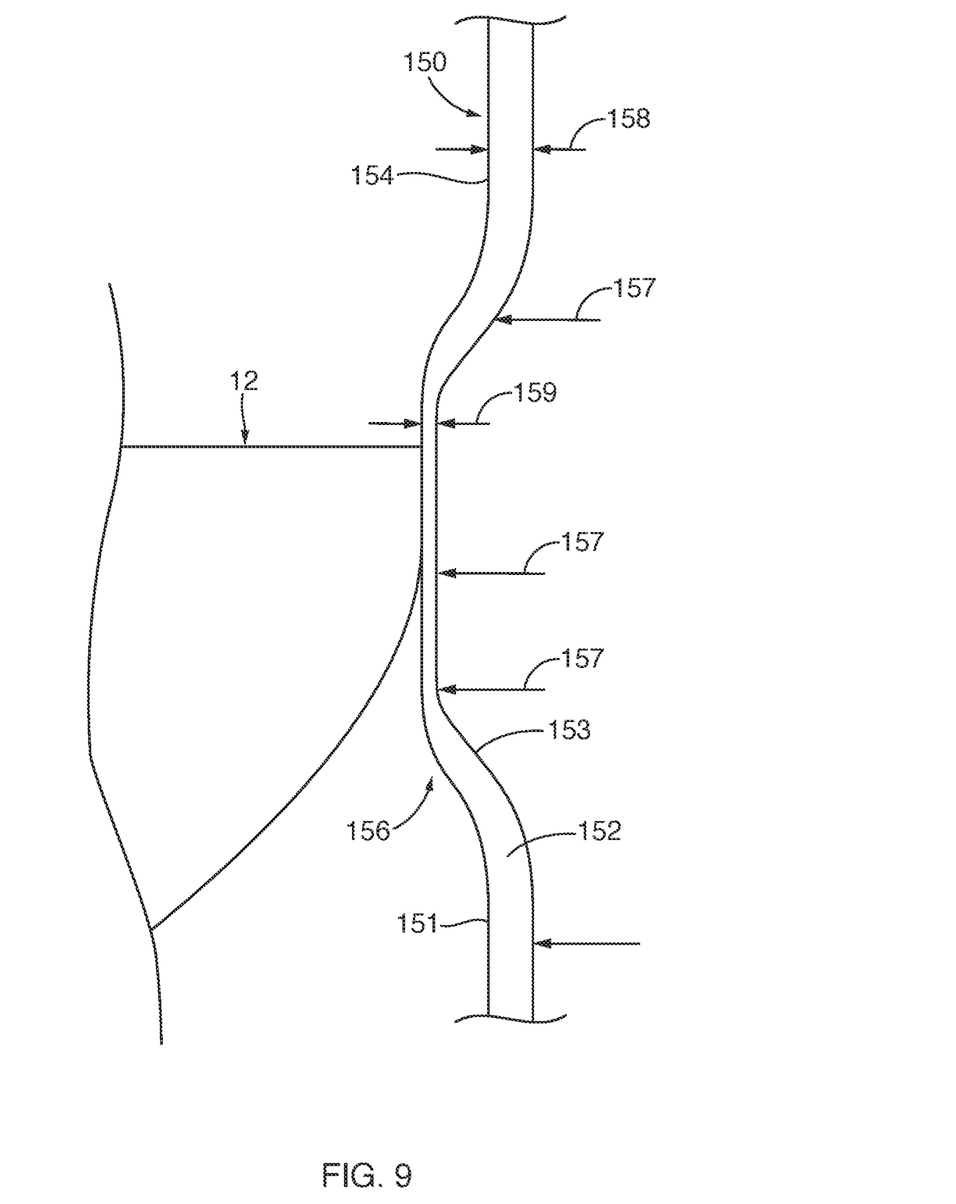
FIG. 9 is an enlarged view of another embodiment of an inflatable member, depicting a portion of the inflatable member biased against the implant such that the inflatable member includes various thicknesses that change an inflation profile of the inflatable member, according to another embodiment of the present invention.

Now with reference to FIG. 9, another embodiment of an inflatable member 150 extending to define a bore 151 is provided. In this embodiment, the inflatable member 150 may include a wall 152 with an inner surface 154. The inflatable member 150 also may define an interior chamber 153, the interior chamber sized and configured to be filled with fluid or released of the flued to respectively inflate or deflate the inflatable member 150. The inner surface 154 of the inflatable member 150 may be sized and configured to contact and engage the implant 12, similar to previous embodiments. Further, in this embodiment, the inner surface 154 may extend with a topological geometric variation 156 that may be sized and configured to hold the implant 12 to the inflatable member 150. Such topological geometric variation 156 may be sized and configured to extend in a convex manner or a concave manner, upon inflation of the inflatable member 150. In one embodiment, the topological geometric variation 156 may be employed in the wall 152 with multiple chambers within the inflatable member 150, the chambers sized and configured to provide such variation 156 upon inflating the inflatable member 150. In another embodiment, the wall 152 may extend with a variation in thickness. For example, the wall 152 may extend with a first thickness 158 and a second thickness 159, the second thickness 159 being less than the first thickness 158. Due to the second thickness 159 being smaller than the first thickness 158 of the wall 152, the wall 152 along the second thickness 159 may radially expand or radially displace further inward into the bore 151 than the wall 152 along the first thickness 158, upon inflation of the inflatable member 12 to provide an inflation force, as indicated by arrow 157, against the implant 12. In this manner, the wall 152 of the inflatable member 150 may extend to define a varied thickness along its length to control the radial displacement of portions of the inner surface 154 of the inflatable member 150. Further, the thickness of the wall 152 may vary along predetermined portions of the wall for more effectively positioning the implant 12 within the bore 151 of the inflatable member 150. As such, the positioning of the implant 12 within the bore 151 of the inflatable member 150 may be a replication of muscle orientation along, for example, the ostium of the left atrial appendage in the heart, which may generate variations in stretching of the inner surface 154 to vary the fine radial displacement applied to the implant 12.

The inflatable member may be formed of a polymeric material, such as, silicone, rubber, polydimethylsiloxane (PDMS), or any other suitable polymeric material with elastic properties. Further, the inflatable member may be formed from a fabric material, such as a woven, reinforced and/or embedded fabric material, or combinations of a polymeric material and a fabric material, or any other suitable inflatable material.

While the invention may be susceptible to various modifications and alternative forms, specific embodiments have been shown by way of example in the drawings and have been described in detail herein. Further, the structural features of any one embodiment disclosed herein may be combined or replaced by any one of the structural features of another embodiment set forth herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A durability testing fixture configured to test a medical device, the medical device having a hub and a framework such that the framework extends radially from the hub, the fixture comprising:
   a stabilizing member;
   an inflatable member positioned adjacent the stabilizing member, the inflatable member extending to define a bore therein such that the bore is sized and configured to position the medical device within the bore so that an inner surface of the inflatable member that defines the bore engages an outer radially extending surface of the medical device, the inflatable member configured to receive and release a fluid so that the inflatable member is respectively inflatable and deflatable to radially displace the inner surface of the bore; and
   a pressure controller coupled to the inflatable member, the pressure controller configured to control inflation and deflation of the inflatable member to radially displace the inner surface of the bore and to apply a force directly along the outer radially extending surface of the medical device;
   wherein the inflatable member extends with a wall, the wall extending with a first thickness and a second thickness, the second thickness being smaller than the first thickness.

2. The durability testing fixture of the claim 1, wherein the bore is sized and configured to surround the outer radially extending surface of the medical device such that the inner surface radially engages the medical device.

3. The durability testing fixture of claim 1, wherein the inflatable member extends with multiple chambers defined therein.

4. The durability testing fixture of claim 1, wherein the inflatable member comprises one or more sensors associated therewith.

5. The durability testing fixture of claim 1, wherein, upon the inflatable member being inflated, the inflatable member exhibits a convex structure along the second thickness of the wall of the inflatable member.

6. The durability testing fixture of claim 1, wherein, upon the inflatable member being inflated, the inflatable member exhibits a convex structure along the inner surface of the inflatable member.

7. The durability testing fixture of claim 1, wherein, upon the inflatable member being inflated and deflated by the pressure controller, the bore of the inflatable member is moved between a first diameter and a second diameter.

8. A testing system for testing a medical device, the medical device having a hub and a framework such that the framework extends radially from the hub, the testing system comprising:
   a computing device with one or more processors;
   a pressure controller coupled to the computing device, the pressure controller including a fluid line associated therewith;
   a stabilizing member; and
   an inflatable member positioned adjacent the stabilizing member, the inflatable member extending to define a bore therein such that the bore is sized and configured to position the medical device within the bore so that an inner surface of the inflatable member that defines the bore engages an outer radially extending surface of the medical device, the inflatable member configured to receive and release a fluid so that the inflatable member is respectively inflatable and deflatable to radially displace the inner surface of the bore;

wherein the pressure controller is coupled to the inflatable member with the fluid line, the pressure controller configured to control inflation and deflation of the inflatable member to radially displace the inner surface of the bore and to apply a force directly along the outer radially extending surface of the medical device; and wherein the inflatable member extends with a wall, the wall extending with a first thickness and a second thickness, the second thickness being smaller than the first thickness; and wherein, upon the inflatable member being inflated, the inflatable member exhibits a convex structure along the second thickness of the wall of the inflatable member.

9. The testing system of the claim 8, wherein the bore is sized and configured to surround the outer radially extending surface of the medical device such that the inner surface radially engages the medical device.

10. The testing system of claim 8, wherein the inflatable member extends with multiple chambers defined therein.

11. The testing system of claim 8, wherein the inflatable member comprises one or more sensors associated therewith.

12. The testing system of claim 8, wherein, upon the inflatable member being inflated, the inflatable member exhibits a convex structure along the inner surface of the inflatable member.

13. The testing system of claim 8, wherein, upon the inflatable member being inflated and deflated by the pressure controller, the bore of the inflatable member is moved between a first diameter and a second diameter.

14. A method for testing the durability of a medical device, the method comprising:
providing a fixture including a stabilizing member and an inflatable member, the inflatable member positioned adjacent the stabilizing member, the inflatable member extending to define a bore therein;
positioning the medical device within the bore of the inflatable member so that an inner surface of the inflatable member that defines the bore engages an outer radially extending surface of the medical device;
radially displacing the inner surface of the bore with a pressure controller coupled to the inflatable member such that fluid inflates and deflates the inflatable member to apply a radial force directly along the outer radially extending surface of the medical device; and
sequentially inflating and deflating multiple chambers defined in the inflatable member.

15. The method according to claim 14, wherein the radially displacing comprises repeatedly radially displacing the inner surface of the inflatable member to repeatedly radially displace portions of the medical device.

16. The method according to claim 14, further comprising sensing a radial force placed upon the medical device with one or more sensors associated with the inflatable member.

17. The method according to claim 14, further comprising controlling a cycle rate by which the inflatable member is inflated and deflated and tracking the number of cycles with a computing device.

* * * * *